United States Patent [19]

Tommasini et al.

[11] Patent Number: 5,264,700

[45] Date of Patent: Nov. 23, 1993

[54] METHOD FOR TELECAMERA-CHECKING PRODUCTS WRAPPED WITH TRANSPARENT MATERIAL

[75] Inventors: Bruno Tommasini; Armando Neri, both of Bologna, Italy

[73] Assignee: G.D Società per Azioni, Bologna, Italy

[21] Appl. No.: 869,729

[22] Filed: Apr. 17, 1992

[30] Foreign Application Priority Data

Apr. 19, 1991 [IT] Italy .............................. B091A000123

[51] Int. Cl.$^5$ ...................... G01N 21/00; G65B 57/02
[52] U.S. Cl. ................................. 250/372; 250/359.1; 53/53; 209/536; 209/578; 209/587; 358/110
[58] Field of Search ............... 209/536, 576, 577, 578, 209/587; 358/106, 110; 250/372, 359.1; 53/53

[56] References Cited

U.S. PATENT DOCUMENTS 4,053,056 10/1977 Day ..................................... 209/536
5,101,609 4/1992 Cook ....................................... 53/53

Primary Examiner—Carolyn E. Fields
Attorney, Agent, or Firm—Ladas & Parry

[57] ABSTRACT

A method for telecamera-checking of products (1) wrapped with transparent material, in particular packets of cigarettes, in which a product (1) wrapped with transparent material is illuminated by an ultraviolet lamp (6) and is scanned by a telecamera (4), which feeds an image of the product (1) into an image processor (5) to verify the soundness of the wrapped product (1) by processing the image in accordance with a determined programme.

12 Claims, 1 Drawing Sheet

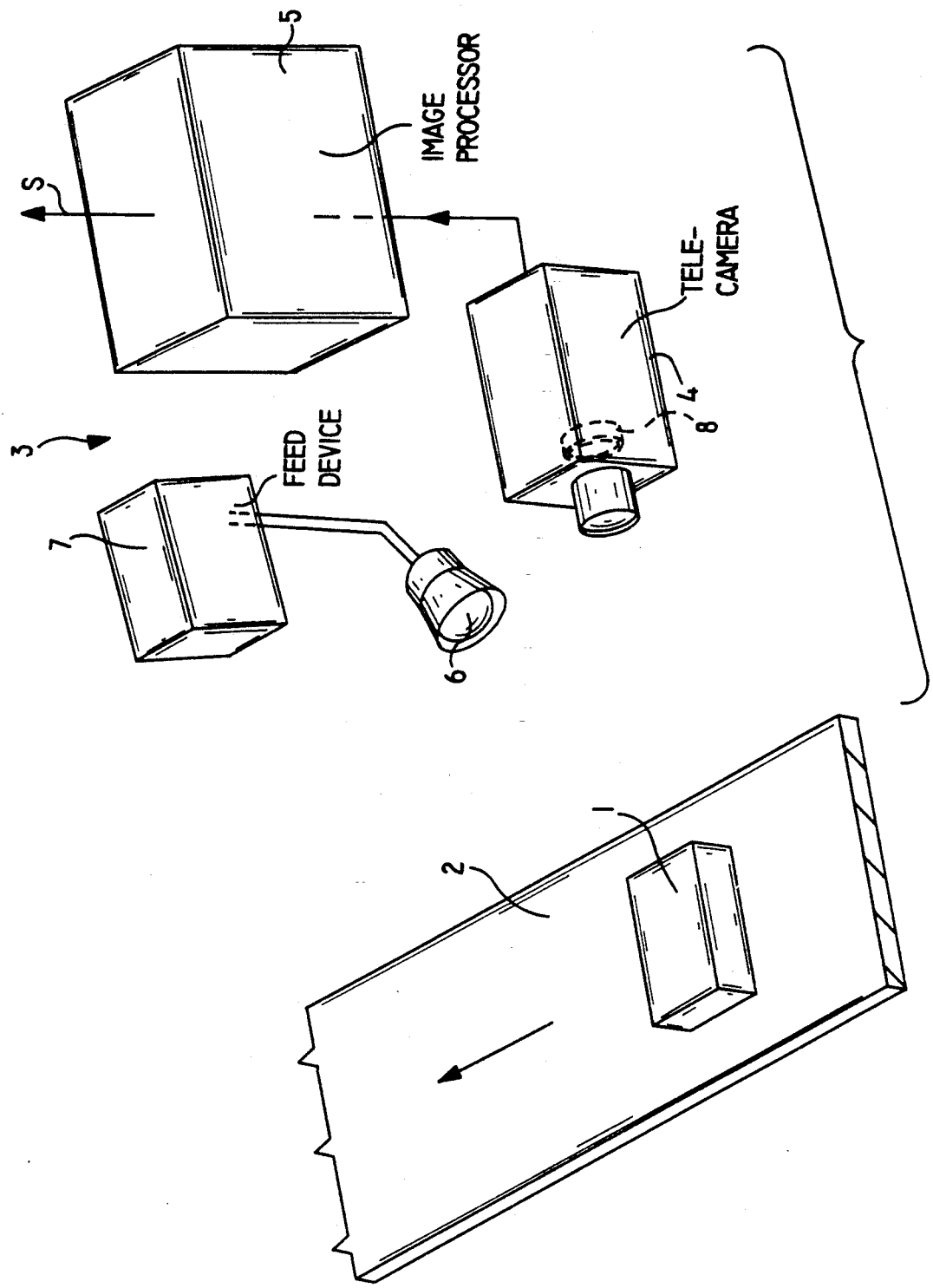

METHOD FOR TELECAMERA-CHECKING PRODUCTS WRAPPED WITH TRANSPARENT MATERIAL

This invention relates to a method for telecamera-checking products wrapped with transparent material.

The method in the present invention can be advantageously applied in the field of packeting machines in general and cigarette packeting machines in particular, to which the ensuing description will explicitly refer, but without on this account losing its generality.

The checks conducted on packets leaving cigarette packeting machines tend to be made when the packets are as close as possible to completion. In this respect, a check conducted before packet completion would not detect any damage suffered by the packets during their handling subsequent to the check. Consequently packet checking, normally performed with one or more telecameras, should in theory be conducted on finished packets, i.e. on packets already provided with their outer wrapping of cellophane or other corresponding thermoweldable transparent material.

This is not possible in the current state of the art, because to enable them to be scanned by a telecamera the packets are illuminated by a white light beam, which is reflected by the transparent outer wrapping, thereby preventing checking of the underlying packet. Consequently, at present, packet checking is effected before the packets enter the cellophane wrapping machine, with the result that any damage suffered by the packets within the cellophane wrapping machine cannot be detected, so that damaged packets cannot be rejected.

The object of the present invention is to provide a method for enabling telecamera detection of products in general, and cigarette packets in particular, which are already wrapped with a transparent material.

According to this invention, a method for telecamera-checking production wrapped with a transparent material is disclosed, the method comprising: illuminating a product wrapped with transparent material, scanning the illuminated product by a telecamera to produce a product image, and feeding this image into an image processor to verify the soundness of the wrapped product by processing the image in accordance with a determined programme, characterised in that the illumination of the wrapped product is effected by a light source the light emission of which has a frequency prevalently outside the frequency range of visible light.

Preferably said light source has a light emission prevalently within the ultraviolet range.

According to a preferred embodiment of the present invention said light source is a Wood lamp.

BRIEF DESCRIPTION OF THE DRAWING

The invention is described hereinafter with reference to the accompanying figure, which represents a schematic perspective view, partly in block form, of a preferred but non-limiting embodiment thereof.

In the accompanying figure, reference numeral 1 indicated a packet of cigarettes fed along a determined path by a conveyor 2 and provided with an outer wrapping of transparent material such as cellophane.

The feed path of packet 1 extends through a checking station 3, in which the soundness of packet 1 is checked by a telecamera 4 which scans packet 1 and produces an image which is fed by telecamera 4 to an image processor 5 of the known type, which verifies in known manner the soundness of packet 1 by processing the image in accordance with a determined programme. In order to make scanning of the wrapped product 1 by telecamera 4 possible, packet 1 is illuminated by a lamp 6 connected to a feed device 7.

If the lamp 6 used is a normal white light lamp, the reflection producted by the transparent wrapping material prevents scanning of the packets 1 by telecamera 4. In contrast, it has been found that if the lamp 6 used is a lamp having a light emission frequency prevalently outside the visible light range, not only does the said reflection not take place, but packet 1 remains perfectly visible to the telecamera 4, which is a normal commercial telecamera having, as is normally the case, a passband wider than that of the human eye, and is hence able to perceive the light radiation reflected by packet 1 even when the frequency of this radiation is prevalently outside the visible light frequency range.

The best results have been obtained with emissions prevalently within the ultraviolet range, and in particular when using a Wood lamp as lamp 6.

In general, in the case in which, as in the illustrated example, packets 1 are checked while moving, the lamp used is a stroboscopic lamp, which enables fixed images to be formed by telecamera 4.

Given the still existing difficulty of powering lamps of prevalently ultraviolet emission in such a manner as to obtain intermittent lighting, and the cost of such lamps for intermittent use, the stroboscopic effect substantially necessary for scanning moving packets 1 being preferably achieved by an intermittently opening mechanical or electronic shutter mounted on telecamera 4 or, in accordance with a non-illustrated variation, interposed between lamp 6 and packets 1.

Shutter 8 can obviously be eliminated if packet 1 is at rest or conveyor 2 is a stepping conveyor.

As stated, the image of packet 1 obtained by telecamera 4 is fed to the image processor 5 in the known manner, which using a determined programme compares the image of packet 1 under examination with a previously memorized reference image of a sound packet. If processor 5 detects a substantially difference between the image of packet 1 under examination and the reference image, it emits a reject signal S for operating a known reject device (not shown).

It should be noted that lamp 6 could be replaced by a wide-band light source by interposing—between packets 1 to be checked and this light source—a high-pass optical filter (also not shown and in fact forming part of the light source itself) able to filter the light and direct exclusively or prevalently ultraviolet light towards the packets 1.

We claim:

1. A method for telecamera-checking products wrapped with transparent material, the method comprising illuminating a product (1) wrapped with transparent material, scanning the illuminated product (1) by a telecamera (4) to produce an image of the product (1), and feeding this image into an image processor (5) to verify the soundness of the wrapped product (1) by processing the image in accordance with a determined program, characterised in that the illumination of the wrapped product, through the transparent material, (1) is effected by a light source (6) the light emission of which has a frequency prevalently outside the visible light frequency range.

2. A method as claimed in claim 1, characterised in that said light source (6) has a light emission prevalently within the ultraviolet range.

3. A method as claimed in claim 2, characterised in that said light source (6) is a Wood lamp.

4. A method as claimed in claim 2, characterised in that said light source is a wide-band lamp, a high-pass optical filter being interposed between said lamp and the products (1) to be checked.

5. A method as claimed in claim 2, characterised in that said scanning occurs during the movement of the products (1) along a predetermined path, the method further comprising the creation of a stroboscopic effect to enable aid telecamera (4) to provide fixed images of the moving products (1).

6. A method as claimed in claim 1 characterised in that said light source (6) is a Wood lamp.

7. A method as claimed in claim 6, characterised in that said scanning occurs during the movement of the products (1) along a predetermined path, the method further comprising the creation of a stroboscopic effect to enable said telecamera (4) to provide fixed images of the moving products (1).

8. A method as claimed in claim 1 or 2, characterised in that said light source is a wide-band lamp, a high-pass optical filter being interposed between said lamp and the products (1) to be checked.

9. A method as claimed in claim 8, characterised in that said scanning occurs during the movement of the products (1) along a predetermined path, the method further comprising the creation of a stroboscopic effect to enable said telecamera (4) to provide fixed images of the moving products (1).

10. A method as claimed in claim 1, characterised in that said scanning occurs during the movement of the products (1) along a predetermined path, the method further comprising the creation of a stroboscopic effect to enable said telecamera (4) to provide fixed images of the moving products (1).

11. A method as claimed in claim 10, characterised in that said stroboscopic effect is achieved by mounting an intermittently opening mechanical or electronic shutter (8) on the telecamera (4).

12. A method as claimed in claim 1, wherein the frequency of the light emission is chosen to produce reduced reflection from the transparent material than that produced by white light, and to be within the image detection bandwidth of the telecamera.

* * * * *